United States Patent [19]

Kuo et al.

[11] 4,245,044

[45] Jan. 13, 1981

[54] FAT EMULSION PYROGENICITY TEST

[75] Inventors: Harng-Shen Kuo, Pinole; Shantilal C. Mutha, El Cerrito; Charles R. Thompson, Walnut Creek, all of Calif.

[73] Assignee: Cutter Laboratories, Inc., Berkeley, Calif.

[21] Appl. No.: 8,462

[22] Filed: Feb. 1, 1979

[51] Int. Cl.$^3$ ............................................. C12Q 1/04
[52] U.S. Cl. .................................... 435/34; 23/230 B
[58] Field of Search ...................... 435/34; 23/230 B; 252/408; 424/12, 101

[56] References Cited

U.S. PATENT DOCUMENTS

| | | | |
|---|---|---|---|
| 4,038,029 | 7/1977 | Teller et al. | 23/230 B |
| 4,096,091 | 6/1978 | Hopkins | 435/34 X |
| 4,107,077 | 8/1978 | Sullivan et al. | 435/34 X |

*Primary Examiner*—Thomas G. Wyse
*Attorney, Agent, or Firm*—James A. Giblin

[57] ABSTRACT

Low concentration pyrogens in fat emulsions can be determined by using Limulus lysate test procedures. A preferred lysate was observed to have a relatively low calcium ion concentration.

7 Claims, No Drawings

FAT EMULSION PYROGENICITY TEST

BACKGROUND OF THE INVENTION

1. Field

This disclosure is concerned generally with the testing of materials for the presence of pyrogens (e.g. bacterial endotoxins) and specifically with a pyrogenicity test for fat emulsion intended for intravenous administration.

2. Prior Art

Pharmaceutical solutions are routinely tested for the presence of pyrogens (fever producing substances) using either the U.S.P. rabbit test or, more recently, a coagulation test which involves use of a lysate of the amoebocyte blood cells of the horseshoe crab, Limulus sp. This latter test, commonly referred to as the Limulus lysate test, is based on the observation that the lysate will form a gel in the presence of very low concentrations (e.g. nanogram levels) of pyrogens such as bacterial endotoxins. The general Limulus lysate test procedure is described in detail in an article by E. Thye Yin et al, Biochem. Biophys. Acta, Vol. 261, pp. 284-285 (1972). Various additives for improving the sensitivity of Limulus lysates are disclosed in a recent patent to R. E. Hopkins, U.S. Pat. No. 4,096,091.

Recently, pharmaceutically useful fat emulsions have become available to supplement intravenous solutions of various carbohydrates and amino acids. Although the carbohydrate and amino acid solutions can be tested for pyrogenicity using the U.S.P. rabbit test, or the Limulus lysate test, it has been found that when fat emulsions are tested by the U.S.P. rabbit test a false positive may occur as a result of a thermogenic response in the rabbits. See, for example, the study by G. F. Lambert et al, Am. J. Physiol. 164:490-496 (1951). See also articles by R. Grant, Amer. J. Physiol. 173:246-253 (1953) and S. W. Thompson et al, Amer. J. Clin. Nutrition 16:43-61 (1965).

We have found that the uncertainities (false positives) associated with using the U.S.P. rabbit test for fat emulsions can be avoided with a test procedure which, prior to our application, had not been associated with aqueous fat emulsions. Details of our test procedure, which appears to be more sensitive than the U.S.P. rabbit test on fat emulsions, are described below.

SUMMARY OF THE INVENTION

Our method for testing for the presence of pyrogens in a fat emulsion comprises the steps of incubating the fat emulsion with a lysate of amebocyte blood cells of the horseshoe crab (Limulus sp., esp. *Limulus polyphemus*) and determining whether gelation of at least some of the lysate constituents occurs. In one embodiment, a protein-containing fluid (the lysate) of amebocyte blood cells of the crab is incubated with the aqueous fat emulsion at $37°\pm1°$ C. for $60\pm5$ minutes and the presence or absence of a gel is determined. In a preferred embodiment, contrary to some past suggestions, our preferred lysate does not contain calcium ions in an amount above that naturally occurring in the crab amebocytes. Our preferred lysate can determine pyrogen concentrations as low as 0.03 ng/ml of E. coli endotoxin in aqueous fat emulsions.

SPECIFIC EMBODIMENTS

In general, our test for pyrogens in aqueous fat emulsions is similar to the Limulus amebocyte lysate (LAL) test presently used for testing for pyrogens in true aqueous solutions intended for intravenous administration. The lysate can be obtained commercially or can be made and standardized by known methods. The actual test involves mixing a given amount (e.g. 0.1 ml) of the aqueous fat emulsion to be tested with a given amount (e.g. 0.1 ml) of the lysate and then allowing the mixture to incubate at a given temperature for a given time. The test typically takes place in test tubes placed in a water bath at $37°\pm1°$ C. If pyrogens (e.g. bacterial endotoxins) are present in the fat emulsion sample, a gel will form within a given amount of time (e.g. 60 mins.). Formation of a gel can be readily determined by simply inverting the incubation test tube and then recording the results according to a standard such as the following:

+Firm Gel—gel remains intact and does not flow down sides of tube.

−No Gel or Soft Gel—sample remains liquid or globular and flows down side of tube.

In the studies described below, the fat emulsion used for pyrogen testing was Intralipod ® 10% IV fat emulsion, an intravenously administratable product of Cutter Laboratories, Inc., Berkeley, California. To determine if the Limulus Test could be used as an alternate pyrogen test for the Intralipod ® product, a study comparing the rabbit and Limulus tests was carried out. The fat emulsion tested below is described in U.S. Pat. No. 3,169,094 to Wretlind.

EXAMPLES

E. coli endotoxin obtained from Difco (Pyrotrol TM positive control) was used as a pyrogen source. Limulus lysate was obtained from Haemachem Inc., lot no. 27A1, (Lysate sample 1), Association of Cape Cod, Woods Hole, Massachusetts, lot no. 205, (Lysate sample 2), and Mallinckrodt, St. Louis, Missouri, lot no. 7ZGB, (Lysate sample 3). The E. coli endotoxin was standardized against a known Bureau of Biologics standard. The E. coli endotoxin was used because it is the most potent commercially available endotoxin.

The Intralipid ® 10% IV fat emulsion was spiked with the E. coli endotoxin to result in the following endotoxin levels: 0.03, 0.06, and 0.12 ng/ml. An unspiked sample of Intralipid ® fat emulsion was used as control.

All Intralipid ® emulsion samples were also pyrogen tested according to the U.S.P. XIX rabbit test procedure (U.S. Pharmacopeia XIX, p. 613, 1975). Each rabbit received 10 ml per kg of the solution to be tested. In addition, all the spiked Intralipid ® emulsion and control samples were tested by the Limulus Test using all three sample lysates.

The test results are shown in Table I. Of the three lysates evaluated to detect E. coli endotoxin in spiked Intralipid ® samples, one was found to be especially sensitive. The other lysates were able to detect only higher concentrations of endotoxin or were not consistent. Twenty aliquots of each spiked sample were tested with each of the three lysates.

TABLE I.
RESPONSE OF ENDOTOXIN SPIKED INTRALIPID® TO VARIOUS LYSATES

| Sample | Endotoxin Concentration | Lysate Sample No. 1 + | 1 − | 2 + | 2 − | 3 + | 3 − |
|---|---|---|---|---|---|---|---|
| 10% Intralipid® | | | | | | | |
| Lot 1 | 0.12 ng/ml | 20 | 0 | 20 | 0 | ND | |
| Lot 2 | 0.06 ng/ml | 20 | 0 | 20 | 0 | ND | |
| Lot 3 | 0.06 ng/ml | 20 | 0 | 0 | 20 | 14 | 6 |
| Lot 2 | 0.03 ng/ml | 18 | 2 | 0 | 20 | ND | |
| Lot 3 | 0.03 ng/ml | 19 | 1 | ND | | 0 | 20 |
| Control | | | | | | | |
| Lot 1 | 0.00 ng/ml | 0 | 20 | ND | | ND | |
| Lot 2 | 0.00 ng/ml | 0 | 20 | ND | | ND | |
| Lot 3 | 0.00 ng/ml | 0 | 20 | ND | | ND | |

(+ = Firm Gel; − = No Gel; ND = Not Done)

COMPARISON OF RABBIT AND LAL PYROGEN TESTING OF INTRALIPID® FAT EMULSION

Each test group consisted of three rabbits which were administered 10 ml/kg of Intralipid® fat emulsion spiked with endotoxin. Samples requiring a re-test according to the U.S.P. XIX test were considered to have failed this test.

The test results of E. coli endotoxin dose response in rabbits are shown in Table II. All E. coli endotoxin levels were also tested by the LAL test procedure and gave positive results. A positive Limulus result, as above, was a gel (+) which remains intact and does not flow down the sides of the tube when inverted as in the case of a negative (−) result.

The 0.12 ng/ml level was only tested in one rabbit test since the temperature rise was unequivocal and 20/20 LAL tests were positive. The 0.06 ng/ml level produced a pyrogenic response in 3/5 rabbit tests and was positive in 100/100 LAL tests. The 0.03 ng/ml produced a pyrogenic response in 2/5 rabbit tests and was positive in 56/60 LAL tests. From these results it was concluded that 0.06 ng/ml was the lowest level that could be detected in a rabbit test and that a level as low as 0.03 ng/ml could be detected using the LAL test.

The Limulus test procedure was thus determined to be an acceptable alternate assay to the rabbit pyrogen test for detection of endotoxin and endotoxin-like material in Intralipid® especially using lysate sample 1.

TABLE II.
COMPARISON OF RABBIT AND LAL PYROGEN TESTING OF INTRALIPID® FAT EMULSION

| Intralipid® fat emulsion Lot # | Endotoxin ng/ml | Rabbit Test °C. Rise #1 | #2 | #3 | Pass/ Fail | LAL Test Positive/ Negative (20 Tests) |
|---|---|---|---|---|---|---|
| 1 | 0.12 | 0.6, | 1.1, | 1.4 | Fail | Positive (20/20) |
| 2 | 0.06 | 0.7, | 0.5, | 0.5 | Fail | Positive (20/20) |
| | | 0.6, | 0.4, | 1.0 | Fail | Positive (20/20) |
| 3 | 0.06 | 0.6, | 0.6, | 0.1 | Fail | Positive (20/20) |
| | | 0.4, | 0.0, | 0.2 | Pass | Positive (20/20) |
| 4 | 0.06 | 0.0, | 0.1, | 0.5 | Pass | Positive (20/20) |
| 2 | 0.03 | 0.5, | 0.1, | 0.5 | Pass | Positive (18/20) |
| | | 0.3, | 0.3, | 0.0 | Pass | |
| 3 | 0.03 | 0.6, | 0.2, | 0.2 | Fail | Positive (19/20) |
| 4 | 0.03 | 0.4, | 0.4, | 0.5 | Pass | Positive (20/20) |
| | | 0.8, | 0.3, | 0.4 | Fail | |
| 1 | 0 | 0.0, | 0.0, | 0.0 | Pass | Negative (20/20) |
| 2 | 0 | 0.0, | 0.0, | 0.0 | Pass | Negative (20/20) |
| 3 | 0 | 0.0, | 0.0, | 0.0 | Pass | Negative (20/20) |
| 4 | 0 | — | | | | Negative (20/20) |

PYROGEN TESTING OF THE AQUEOUS PHASE OF FAT EMULSION

Having shown that the Limulus test was an acceptable alternate for detecting pyrogen activity in the fat emulsion, we then centrifuged the fat emulsion spiked with endotoxin and tested the aqueous phase for pyrogenicity. Administration to rabbits of the separated aqueous phase of the fat emulsion should have avoided the thermogenic response caused by the fat and would thus provide a true test of pyrogenic activity.

Initially, bottles of Intralipid® 10% fat emulsion (Lot 195271) were spiked with Difco E. coli Endotoxin (Lot No. 509711) at 0, 0.12, 0.06 and 0.03 ng/ml levels. Three additional bottles were tested at the 0.03 ng/ml level with a second control. Approximately 350 ml from each bottle were transferred to 500 ml polycarbonate bottles and centrifuged at 13,700 XG at 4° C. for two hours. Analysis of the aqueous phase showed that a major amount (97%) of the fat had been removed and that the concentration of phospholipid had not changed. The aqueous phase was tested for pyrogenicity by the U.S.P. rabbit and LAL methods. Samples of the uncentrifuged emulsion were tested at the same time. The results are presented in Table III.

TABLE III.
PYROGEN TESTING OF INTRALIPID® EMULSION AND ITS AQUEOUS PHASE

| Bottle No. | Sample | Endotoxin Level (ng/ml) | Temp Rise in 3 Rabbits (°C.) | Total | Pass/ Fail | LAL |
|---|---|---|---|---|---|---|
| 1 | Emulsion | 0 | 0.0, 0.0, 0.0 | 0.0 | Pass | Negative |
| | Aqueous | | 0.0, 0.0, 0.0 | 0.0 | Pass | Negative |
| 2 | Emulsion | 0.12 | 0.5, 0.5, 1.0 | 2.0 | Fail | Positive |
| | Aqueous | | 0.2, 0.5, 1.2 | 1.9 | Fail | Positive |
| 3 | Emulsion | 0.06 | 0.2, 0.6, 0.7 | 1.5 | Fail | Positive |
| | Aqueous | | 0.5, 0.5, 0.6 | 1.6 | Fail | Positive |
| 4 | Emulsion | 0.03 | 0.0, 0.2, 0.5 | 0.7 | Pass | Positive |
| | Aqueous | | 0.0, 0.6, 0.6 | 1.2 | Fail | Positive |
| 5 | Emulsion | 0 | 0.0, 0.0, 0.0 | 0.0 | Pass | Negative |
| | Aqueous | | 0.0, 0.0, 0.0 | 0.0 | Pass | Negative |
| 6 | Emulsion | 0.03 | 0.0, 0.2, 0.3 | 0.5 | Pass | Positive |
| | Aqueous | | 0.1, 0.3, 0.5 | 0.9 | Pass | Positive |
| 7 | Emulsion | 0.03 | 0.1, 0.1, 0.2 | 0.4 | Pass | Positive |
| | Aqueous | | 0.0, 0.1, 0.3 | 0.4 | Pass | Positive |
| 8 | Emulsion | 0.03 | 0.0, 0.8, 0.9 | 1.7 | Fail | Positive |
| | Aqueous | | 0.2, 0.2, 0.2 | 0.6 | Pass | Positive |

The results show that pyrogen activity can be detected in the aqueous phase at the same level as in the emulsion. In order to avoid the thermogenic response, an acceptable alternative would be to test in rabbits the aqueous phase of the emulsion. This procedure could be used for testing lots that have produced a temperature rise (possible false positive due to thermal response) in rabbits.

The above results also demonstrate that the Limulus test is more sensitive than the U.S.P. rabbit test in testing for pyrogens in fat emulsions since it consistently detected concentrations as low as 0.03 ng/ml endotoxin.

FURTHER STUDIES

In an effort to understand why lysate sample no. 1 appeared to provide greater assay sensitivity and consistency, all three lysates were subjected to atomic absorption analysis for both magnesium ion concentration and calcium ion concentrations. It had been known (see for example U.S. Pat. No. 4,096,091) that magnesium ions were considered useful as catalytic additives for Limulus lysates. In addition, it was known that in some cases, calcium has been added as a gelation potentiator (see above cited patent). The results of the atomic absorption analysis studies are summarized below.

TABLE IV.

| Metal ion | Lysate Sample | | |
|---|---|---|---|
| (in ppm) | #1 | #2 | #3 |
| Mg++ | 0.8 | 0.9 | 1.0 |
| Ca++ | 10 | 110 | 135 |

Although the magnesium concentrations of all three samples appeared to be about the same, it can be seen from the results in Table IV that there is about a tenfold difference in calcium concentrations between the lysate sample #1 and samples #2 and #3. Although the exact mechanism whereby lysate sample #1 gave greater test sensitivity is not understood, lysate sample #1, having a calcium ion concentration close to that which would be expected to occur naturally in the amebocyte cells, is our preferred lysate.

Since the invention of the above disclosure is subject to variations, it should be understood that the above examples are merely illustrative and that the invention disclosed herein should be limited only by the following claims.

We claim:

1. A method of testing for the presence of pyrogens in an aqueous fat emulsion intended for intraveneous administration which comprises incubating the fat emulsion with a Limulus lysate solution under conditions sufficient to effect gelation of at least some lysate constituents if pyrogens are present in the aqueous fat emulsion at a predetermined concentration.

2. The method of claim 1 wherein the pyrogen is E. coli endotoxin at a predetermined concentration at least as low as about 0.12 ng/ml of aqueous fat emulsion.

3. The method of claim 2 wheren the predetermined concentration of pyrogen is at least as low as about 0.06 ng/ml.

4. The method of claim 3 wherein the predetermined concentration of pyrogen is at least as low as about 0.03 ng/ml.

5. The method of claim 1 wherein the incubation conditions are at a temperature of $37° \pm 1°$ C. for about 60 minutes.

6. The method of claim 1 wherein the concentration of calcium ions is approximately that concentration found naturally in amebocyte cells from which the lysate is prepared.

7. The method of claim 1 wherein, prior to incubation with the lysate, the majority of the fat emulsion is separated from the aqueous emulsion to result in a substantially aqueous remaining portion which portion is then incubated with the lysate.

* * * * *

UNITED STATES PATENT AND TRADEMARK OFFICE
CERTIFICATE OF CORRECTION

PATENT NO. : 4,245,044
DATED : January 13, 1981
INVENTOR(S) : HARNG-SHEN KUO et al It is certified that error appears in the above–identified patent and that said Letters Patent are hereby corrected as shown below:

Column 2, lines 25 and 29, correct the spelling of "Intralipod®" to --Intralipid®-- in both instances.

Signed and Sealed this

Twenty-eighth Day of April 1981

[SEAL]

Attest:

RENE D. TEGTMEYER

*Attesting Officer*  *Acting Commissioner of Patents and Trademarks*